US007858579B2

(12) United States Patent (10) Patent No.: US 7,858,579 B2
Dawson-Scully et al. (45) Date of Patent: Dec. 28, 2010

(54) THERMOPROTECTIVE COMPOSITIONS OF PKG PATHWAY INHIBITORS AND METHOD OF USE THEREOF

(76) Inventors: Kenneth Dawson-Scully, 193 Lakewood Drive, Oakville, Ontario (CA) L6K 1B3; Marla Sokolowski, 87 MacPherson Avenue, Toronto, Ontario (CA) M5R 1W7; Clement Kent, 528 Dovercourt Road, Toronto, Ontario (CA) M6H 2W4; R. Meldrum Robertson, 4490 County Road 8 W, R.R. #2, Napanee, Ontario (CA) K7R 3K7; Gary A. Armstrong, 321 Doris Avenue, Toronto, Ontario (CA) M2N 6C7

(*) Notice: Subject to any disclaimer, the term of this patent is extended or adjusted under 35 U.S.C. 154(b) by 825 days.

(21) Appl. No.: 11/538,645

(22) Filed: Oct. 4, 2006

(65) Prior Publication Data

US 2007/0184044 A1 Aug. 9, 2007

Related U.S. Application Data

(60) Provisional application No. 60/723,527, filed on Oct. 4, 2005.

(51) Int. Cl.
*A01N 37/18* (2006.01)
*A61K 38/00* (2006.01)
(52) U.S. Cl. .................................................. 514/2
(58) Field of Classification Search .................. 514/2
See application file for complete search history.

(56) References Cited

U.S. PATENT DOCUMENTS

| | | | | |
|---|---|---|---|---|
| 5,991,177 | A | 11/1999 | Kaczkowski | 363/62 |
| 6,300,327 | B1 | 10/2001 | Knusel et al. | 514/211 |
| 6,451,837 | B1 | 9/2002 | Baskys | 514/411 |
| 6,476,007 | B2 | 11/2002 | Tao et al. | 514/81 |
| 6,511,800 | B1 | 1/2003 | Singh | 435/4 |
| 6,846,845 | B2 | 1/2005 | Takahashi et al. | 514/675 |

FOREIGN PATENT DOCUMENTS

WO WO 93/08809 * 5/1993

OTHER PUBLICATIONS

Canini, F., et al., "Voltametric assessment of brain nitric oxide during heatstroke in rats," *Neurosci. Lett.*, 1997, 231, 67-70.
Canini, F., et al., "Inhibition of different types of nitric oxide synthase: effect on thermoregulation in the rat exposed to high ambient temperature," *Neurosci. Lett.*, 2001, 316, 45-49.
Chang, C.P., et al., "Aminoguanidine protects against intracranial hypertension and cerebral ischemic injury in experimental heatstroke," *J. Pharmacol. Sci.*, 2004, 95, 56-64.
Corbin, J.D., et al., "Cyclic GMP phosphodiesterase-5: target of sildenafil," *J. Biol. Chem.*, 1999, 274, 13729-13732.
Dostmann, W.R., et al., "Exploring the mechanisms of vascular smooth muscle tone with highly specific, membrane-permeable inhibitors of cyclic GMP-dependent protein kinase ialpha," *Pharmacol. Ther.*, 2002, 93, 203-215.
Fitzpatrick, M.J., et al., "In search of food: exploring the evolutionary link between cGMP-dependent protein kinase (PKG) and behaviour," *Integr. Comp. Biol.*, 2004, 44, 28-36.
Gerstberger, R., "Nitric oxide and body temperature control," *News Physiol. Sci.*, 1999, 14, 30-36.
Glazer, J.L., "Management of heatstroke and heat exhaustion," *American Family Physician*, 2005, 11,2133-2140.
Gulec, G., et al., "Do recurrent febrile convulsions decrease the threshold for pilocarpine-induced seizures? Effects of nitric oxide," *Brain Res. Dev. Brain Res.*, 2001, 126, 223-228.
Gurnett, A., et al., "Purification and molecular characterization of cGMP-dependent protein kinase from apicomplexan parasites," *J. Biol. Chem.*, 2002, 277, 15913-15922.
Jayakar, S.S.., et al., "AMPA receptor regulation mechanisms: future target for safer neuroprotective drugs," *Int. J. Neurosci.*, 2004, 114, 695-734.
Klyueva, Y.A., et al., "Role of nitric oxide and lipid peroxidation in mechanisms of febrile convulsions in Wistar rat pups," *Bull. Exp. Biol. Med.*, 2001, 131, 47-49.
Liu, L., et al., "Voltage-gated ion channels in nociceptors: modulation by cGMP," *J. Neurophysiol.*, 2004, 92, 2323-2332.
White, R.E., "Cyclic GMP and ion channel regulation," *Advances in Second Messenger and Phosphoprotein Research*, 1999, 33, 251-277.
White, R.E., et al., "Potassium channel stimulation by natriuretic peptides through cGMP-dependent dephosphorylation," *Nature*, 1993, 361, 263-266.
Zeng, H., et al., "The slowpoke channel binding protein slob from *drosophila melanogaster* exhibits regulatable protein kinase activity," *Neurosci. Lett.*, 2004, 365, 33-38.
Zhou, X.B., et al., "Protein phosphatase 2A is essential for the activation of $Ca^{2+}$ - activated $K^+$currents by cGMP-dependent protein kinase in tracheal smooth muscle and Chinese hamster ovary cells," l*J. Biol. Chem.*, 1996, 271, 19760-19767.
Zhou, X.B., et al., "Regulation of stably expressed and native BK channels from human myometrium by cGMP-and cAMP-dependent protein kinase," *Pflugers Arch.*, 1998, 436, 725-734.
Ohnishi, K., et al., "The protein kinase inhibitor, H-7, suppresses heat induced activation of head shock transcription factor 1," Molecular and Cellular Biochemistry, 1999, 197, 129-135.
Stoop et al., "Potentiation of transmitter release by ciliary neurotrophic factor requires somatic signaling", Science, Feb. 3, 1995, 267(5198), 695-699.
Osborne, K.A., et al., "Natural behavior polymorphism due to a cGMP-dependent protein kinase of *drosophila*," *Science*, 1997, 277, 834-836.

(Continued)

*Primary Examiner*—Ruth A Davis
(74) *Attorney, Agent, or Firm*—Woodcock Washburn, LLP (57) ABSTRACT

Neural thermoprotective compositions comprising a pharmacological inhibitor of the PKG pathway are described, as are methods of treating patients and providing neural thermoprotection with the same.

15 Claims, 8 Drawing Sheets

OTHER PUBLICATIONS

Patel, A.L., et al., "Activation of guanosine 3',5'-cycle monophosphate (cGMP)-dependent protein kinase in rabbit aorta by nitroglycerin and sodium nitroprusside," *J. Pharmacol. Exp. Ther.*, 1997, 283, 885-893.

Ramirez, J.M., et al., "Long-term effects of prior heat shock on neuronal potassium currents recorded in a novel insect ganglion slice preparation," *J. Neurophysiol.*, 1999, 81, 795-802.

Renger, J.J., "Neuronal polymorphism among natural alleles of a cGMP-dependent kinase gene, foraging, in *drosophila*," J. of Neuroscience, 1999, 19, 1-8.

Robertson, R.M., "Thermal stress and neural function: adaptive mechanisms in insect model systems," *J. of Thermal Biology*, 2004, 351-358.

Sachidhanandam, S.B., et al., "Naltrexone attenuates plasma nitric oxide release following acute heat stress," *Eur. J. Pharmacol.*, 2002, 450, 163-167.

Werrnet, W., et al., "The cDNA of the two isoforms of bovine cGMP-dependent protein kinase," *FEBS Lett.*, 1989, 251(1,2), 191-196.

Schiffmann, S.N., et al., "Modulation of the voltage gated sodium current in rat striatal neurons by DARPP32, an inhibitor of protein phosphatase," *Eur. J. Neurosci.*, 1998, 10, 1312-1320.

Somjen, G.G., "Ion regulation in the brain;implications for pathophysiology," *Neuroscientist*, 2002, 8, 254-267.

Somjen, G.G., "Mechanisms of spreading depression and hypoxic spreading depression-like depolarization," *Physiol. Rev.*, 81, 1065-1096, Jul. 2001.

Taylor, M.S., et al., "Inhibition of a cGMP-dependent protein kinase by the cell-permeable peptide DT-2 reveals a novel mechanism of vasoregulation," *Mol. Pharmacol.*, 2004, 65, 111-1119.

Tryba, A.K., et al., "Hyperthermia modulates respiratory pacemaker bursting properties," *Neurophysiol.*, 2004, 92, 2844-2852.

Wang, J., et al., "Simultaneous binding of two protein kinase to a calcium-dependent potassium channel," *J. Neurosci.*, 1999, 19, RC4, 1-7.

Wang, J.W., et al., "A novel leg-shaking *drosophila* mutant defective in a voltage-gated $K^+$ current and hypersensitive to reactive oxygen species," *J. Neurosci.*, 2000, 20, 5958-5964.

\* cited by examiner

THERMOPROTECTIVE COMPOSITIONS OF PKG PATHWAY INHIBITORS AND METHOD OF USE THEREOF

CROSS-REFERENCE TO RELATED APPLICATION

The application claims priority to U.S. Ser. No. 60/723,527, filed Oct. 4, 2005, the entire disclosure of which is incorporated herein by reference.

FIELD

In one of its aspects, the present invention relates to a neural thermoprotective composition. In another of its aspects, the present invention relates to a method of treating a medical condition using a neural thermoprotective composition. In yet another of its aspects, the present invention relates to a method of providing neural thermoprotection.

BACKGROUND OF THE INVENTION

Over the past few years, extreme summer temperatures have caused an alarming increase in deaths due to hyperthermia. Elevated body temperatures lead to seizures, respiratory distress, brain damage and death (Glazer, 2005). The time between hyperthermic neuronal failure and cell death and permanent thermal damage is brief (Tryba and Ramirez, 2004). Because neural output failure occurs before permanent thermal damage (Tryba and Ramirez, 2004), this narrow window of time is available for the protection and recovery of neural circuit function until return to normal temperatures. Fast neural recovery allows the hyperthermic individual to resume normal pulmonary and cardiac functioning.

As will be outlined further below, it is known that the cGMP-dependent protein kinase G (PKG) pathway may modulate neural potassium (K+) channel activity, and that K+ channel activity may be involved in neural thermoprotection. The involvement of Nitric Oxide (NO) in heatstroke has also been demonstrated, although the nature of this involvement has not been clarified. However, due to the multiplicity of other enzyme pathways which modulate K+ activity and the multiplicity of other channels and other systems which modulate neural thermal response, any relationship between the PKG pathway, K+ channel activity and NO has not been clearly demonstrated.

The PKG enzyme pathway is known, and an outline of the PKG pathway as it is involved in ion channel regulation is provided to assist in understanding:

Briefly, nitric oxide (NO) is produced by various NO synthases (NOS), some of which are activated by a rise in intracellular $Ca^{2+}$. Many NO effects are mediated through direct activation of the soluble guanylyl cyclase (sGC), an enzyme generating the second messenger cyclic guanosine-3',5'-mono-phosphate (cGMP). sGC is stimulated by NO to catalyze the formation of cGMP. cGMP is a cyclic nucleotide second messenger with effects on many pathways, one of which is the cGMP-dependent protein kinase (PKG) enzyme pathway. PKG is an enzyme that transfers a phosphate group from ATP to an intracellular protein, increasing or decreasing its activity.

Both the DNA sequence and protein function of PKG are conserved across the animal kingdom including mammalians. PKG genes have been isolated from various animals spanning a wide variety of taxa ranging from humans (Sandberg et al., 1989) to even the malaria-causing protozoans Plasmodium falciparum (Gurnett et al., 2002). The protein phylogenetic analysis using 32 PKG sequences that include 19 species has shown the highly conserved link between PKG and behaviour in fruit flies, honey bees and nematodes (Fitzpatrick et al., 2004).

It is known that PKG may modulate neural ion channel activity i.e. neural potassium (K+) activity (Renger, 1999). A variety of mechanisms for this effect have been suggested, ranging from direct phosphorylation of the K+ channel by PKG, to the opposing indirect dephosphorylation of the K+ and other channels by phosphatases such as PP2A, which are themselves activated by PKG phosphorylation (Schiffmann et al., 1998; White et al., 1993; White, 1999; Zhou et al., 1996; Zhou et al., 1998). It has been suggested on theoretical grounds that future work in the area of regulation of the PKG pathway might yield some neuroprotective effects but no supporting evidence was provided (Jayakar and Dikshit, 2004).

Effects of cGMP inhibitors on neural ion channels were proposed to lead to pain relief compounds (Liu et al., 2004).

Most research on ion channel direct phosphorylation focuses on the enzyme PKA, which is known to modulate many ion channels (Wang et al., 1999; Zeng et al., 2004). PKA often functions in opposition to PKG, but may function in the same direction.

There is extensive literature related to PKG's known roles in the regulation of smooth muscle and other non-neural tissues, where it may modulate ion channels. A significant amount of medical and pharmaceutical publications relate to such drugs as sildenafil (Viagra) and nitroglycerine for treatment of penile dysfunction or angina (Corbin and Francis, 1999; Patel and Diamond, 1997).

U.S. Pat. No. 6,300,327 to Knusel et al. teaches compositions and methods for use in modulating neurotrophin activity. Neurotrophin activity is modulated by administration of an effective amount of at least one compound which potentiates neurotrophin activity. This patent specifically teaches the potentiation of NT-3 by KT5823, and suggests that this potentiation provides a model for therapeutic intervention in a variety of neuropathological conditions.

U.S. Pat. No. 6,451,837 to Baskys teaches inhibition of the mitogen-activated protein kinase (MAPK) cascade that can lead to nerve cell death. In this context, Okadaic acid, an inhibitor of protein phosphatase was found to increase nerve cell death.

U.S. Pat. No. 6,476,007 to Tao et al. investigated the role of the NO/cGMP signalling pathway in spinal cord pain.

It is known that K+ channel activity may be involved in neural thermoprotection. As canvassed further below, existing literature has considered what happens to neural function during heat-induced malfunction; mechanisms known to provide heat tolerance, such as induction of the heat shock genes and proteins; and investigations into a direct mechanism for neural thermoprotection by K+ channel modulation.

Abnormal K+ concentrations have been associated with various neural failure scenarios such as spreading depression, ischemia, diabetic coma, and hyperthermia (Somjen, 2001; Somjen, 2002).

Recent research by one of the inventors suggests that prior stress down-regulates neuronal K+ currents leading to thermal protection (Robertson, 2004). This was based on findings that prior heat shock provides protective effects against future heat shock and that neuronal K+ currents are effected by prior heat stress (Ramirez et al., 1999).

Other investigations have suggested that K+ channels are involved in neural excitability in response to other stresses such as reactive oxygen (Wang et al., 2000).

It is known that Nitric Oxide (NO) is involved in heatstroke. NO is a pervasive signaling mechanism in the body. One of its functions is to stimulate the PKG pathway, but this is only one of the many routes by which it acts. For instance, NO may be directly toxic to cells, or it may modulate cGMP-dependent ion channels without the involvement of PKG. Thus, prior art showing a correlation of heatstroke with brain NO production does not establish the involvement of the PKG pathway.

For example, NO was shown to be elevated in heatstroke rats (Canini et al., 1997) but a mechanism of involvement in heatstroke was not demonstrated. More recently, it was shown that prior treatments such as Naltrexone, an opiate inhibitor, could reduce NO production during heatstroke, with some beneficial effects such as reduction of body temperature (Sachidhanandam et al., 2002). However, neural protection was not identified as a possible application. Nor was the treatment rapid or responsive to an existing condition: it required administration before heat application.

U.S Pat. No. 6,511,800 to Singh teaches methods for the inhibition of inducible nitric oxide synthesis and the production of NO, and treating of nitric oxide or cytokine mediated disorders.

U.S. Pat. No. 5,990,177 to Brown teaches methods and compositions for stimulating cellular NO synthesis, cGMP levels and PKG activity for the purposes of treating diseases mediated by deficiencies in the NO/cGMP/PKG pathway. Brown does not implicate this system in the treatment of hyperthermic conditions.

In another study, an inhibitor (L-NNA) of NO synthesis administered prior to heat exposure provided small protective effects against febrile convulsions, which the authors attributed to reduction of the directly neurotoxic effects of NO (Klyueva et al., 2001). Again, this is an example of prior treatment, modest protective effects, and no implication of the PKG pathway. Klyueva et al. point out that published data on the role of NO in the pathogenesis of seizures are contradictory: both the anti- and proconvulsant effect of NO have been reported.

Indeed, another study of inhibitors of NO synthesis showed that these reduced heat tolerance (Canini et al., 2001). Another study concluded that NO did not have a pathogenic role in heatstroke at doses given in the study (Gulec and Noyan, 2001). More recently, the inhibitor of NO production aminoguanadine was shown to have some protective effects against heatstroke-induced intracranial hypertension and cerebral ischemic injury by inhibition of cerebral iNOS-dependent NO (Chang et al., 2004).

It has further been observed that NO and cGMP may be involved in thermosensing and thermoregulation, i.e. control of body temperature (Gerstberger, 1999).

There are known treatments for hyperthermia. For example, U.S. Pat. No. 6,846,845 to Takahashi et al. teaches a heat shock protein inducer, which induces heat shock protein in the heart, for preventing or treating ischemic disease or ischemia/reperfusion injury. As pointed out in the patent, heat shock proteins are a family of endogenous protective proteins generated in response to stress, including hyperthermia.

Hyperthermia is currently treated by chilling the person suffering from hyperthermia. This treatment may be insufficient or too late, however, to trigger the neurological recovery necessary to keep the basic systems of the body functioning.

In nature, heat shock protein synthesis protects organisms from sustained high heat conditions over a matter of hours and days. There are currently no therapeutic compounds to prevent hyperthermia, particularly in the short term.

The primary therapy of heatstroke is cooling the patient. The traditional cooling methods such as ice water soaks, immersion in ice baths, and use of cooling blankets as well as application of ice to the groin, neck, and axilla have been used as cooling modalities in heatstroke. Cooling heatstroke patients using these modalities invariably leads to shivering. Diazepam is the drug of choice to decrease shivering and at a dose of 5-10 mg intravenously, abolishes shivering reflexes during cooling. Chlorpromazine (10-25 mg administered slowly IV) also has been recommended to reduce shivering during cooling. Unfortunately, because chlorpromazine may cause hypotension and arrhythmias, and decreases the seizure threshold, it is considered a second-line agent (after diazepam) for controlling shivering associated with cooling.

Dantrolene is the treatment of choice for malignant hyperthermia and has been proposed as a treatment for heatstroke (administered at 1 mg/kg). The mechanism of action appears to involve inhibition of calcium release in skeletal muscle. The major side effects are muscle weakness and nausea. Although effective, studies have shown that there was no significant difference in the number of hospital days in the control and dantrolene treated groups, and mortality and morbidity rates were unchanged. The overall prognosis of heatstroke depends on how fast the cooling therapy is applied to the patients.

Treatment of febrile seizures traditionally consists of continuous or intermittent therapy with anticonvulsants or no therapy. Anticonvulsants have not been proved to prevent subsequent development of febrile seizures nor is there any evidence that febrile seizures cause structural or cognitive damage. Carbamazepine and phenytoin have not been shown to prevent recurrence, whereas phenobarbital reduced the incidence of febrile seizures from 25 per 100 children to five per 100 children. However, hyperactivity and hypersensitivity reactions can occur with this drug. Valproic acid is considered as effective as phenobarbital in preventing recurrence but is associated with several potentially serious adverse effects, such as thrombocytopenia, weight changes and fatal hepatotoxicity. Intermittent treatment may include diazepam, which is associated with a 44 percent reduction in risk per patient year. However, its sedative effects can obscure signs and symptoms of a developing central nervous system infection. Antipyretics have also been used to prevent recurrence, but studies show that they do not have this effect.

SUMMARY OF THE INVENTION

It is an object of the present invention to obviate or mitigate at least one of the above-mentioned disadvantages of the prior art.

Accordingly, in one of its aspects, the present invention provides a neural thermoprotective composition comprising a pharmacological inhibitor of the PKG pathway.

In another of its aspects, the present invention provides a method of treating a medical condition in a patient, which comprises administering to the patient a therapeutically effective amount of a neural thermoprotective composition comprising a pharmacological inhibitor of the PKG pathway.

In another of its aspects, the present invention provides a method of providing neural thermoprotection to a patient comprising administering to a patient a therapeutically effective amount of a pharmacological inhibitor of the PKG pathway.

In yet another of its aspects, the present invention provides the use of a neural thermoprotective composition that includes a pharmacological inhibitor of the PKG pathway to treat a medical condition.

In yet another of its aspects, the present invention provides the use of a pharmacological inhibitor of the PKG pathway to provide neural thermoprotection.

BRIEF DESCRIPTION OF THE DRAWINGS

Embodiments of the present invention will be described with reference to the accompanying drawings, wherein like reference numerals denote like parts and in which:

FIGS. 1 to 2 illustrate hyperthermic failure of both behaviour and NMJ synaptic transmission in $3^{rd}$ instar $for^R$, $for^s$ and $for^{s2}$ Drosophilia larvae.

FIG. 2 illustrates the correlation between genotype and higher temperature at behavioural failure of mouth hook movement.

FIGS. 6 to 7 illustrate motor pattern failure and recovery with increasing temperature of the ventilatory rhythm in adult locusts. Experiments were performed on animals with [HS, N=7] or without [No Heat Shock (NHS), N=6] a 3 hr. heat shock pretreatment at 45° C. (1 hr. recovery) in untreated and 1 µM KT5823-pretreated [HS, N=5; NHS, N=8] preparations.

FIG. 6 illustrates the percentage of animals with arrhythmic events during temperature ramp.

DETAILED DESCRIPTION

Elevated body temperatures can lead to seizures, respiratory distress, brain damage and death (Glazer, 2005). The time between hyperthermic neuronal failure and cell death (Tryba, 2004) provides a window of opportunity for the protection of neural function until return to normal temperatures. The inventors of the subject invention have surprisingly and unexpectedly discovered that inhibition of cGMP-dependent protein kinase (PKG) pathway mediates rapid (within less than three minutes) protection in nervous systems under thermal stress. As shown in the Examples, both genetic and pharmacological manipulations performed by the inventors demonstrate that there is a negative relationship between PKG activity and thermotolerance.

The pharmacological intervention of the present invention provides immediate and significant protection to neurons enduring thermal stress. The invention involves the use of pharmacological inhibitors of the cGMP-dependent protein kinase (PKG) which regulates potassium channel conductances.

The inventors further demonstrate through the Examples that the pathway providing thermoprotection is not sensitive to PKA.

Within the context of the present invention, neural thermoprotection means providing one or more of the following effects:
  increasing the temperature at which neural function becomes abnormal;
  increasing the time to abnormal neural function when exposed to heat;
  reducing the precursor symptoms of neural failure (such as arrhythmias); and
  reducing the time to recovery from abnormal neural function after treatment.

The rapid induction of neural thermoprotection via PKG manipulations in two divergent insect species suggests a widely conserved mechanism, and specifically that future rapid treatments of neural failure during hyperthermic and febrile episodes in humans that involve PKG pathway manipulation.

While other treatments for hyperthermia provide some neural thermoprotection, their modes of action are different than that of the present invention. Having identified a narrowly defined physiological pathway for intervention provides greater scope for future development of more narrowly targeted pharmaceutical agents with potentially fewer side effects.

This invention provides protection as great as the known slow-acting treatments, and may provide more complete neural thermoprotection in some cases. The composition of the present invention may have one or more of the following advantages, as compared to known hyperthermic treatments:
  The increase in temperature at which neural function becomes abnormal is as great as that provided by slow-acting treatments.
  The increase in time to neural failure is as great as or greater than with other treatments (i.e. invention delays neural shut-down when the organism is under heat stress, allowing patient to stay alive and unharmed in higher temperatures.)
  The reduction in precursor abnormalities failure is as great as or greater than with other treatments.
  The reduction in time to recover from neural failure is as great as or greater than with other treatments (i.e. invention shortens neural recovery time following thermal stress, hastening patient's physiological recovery.)

The present invention involves a neural thermoprotective composition that includes a pharmacological inhibitor of the PKG pathway. The inventors of the subject application have surprisingly and unexpectedly discovered that a pharmacological inhibitor of the PKG pathway can provide neural thermoprotection within 3 minutes after administration to the neurons.

A number of pharmacological inhibitors of the PKG pathway are known; these inhibitors effect different points in the enzyme pathway.

A pharmacological inhibitor of the PKG pathway suitable for the present invention, may be a PKG inhibitor, for example: KT5823; (Rp)-8-bromo-PET-cyclic GMPS (Guanosine 3',5'-cyclic Monophosphorothioate, β-Phenyl-1,N²-etheno-8 -bromo-, Rp-Isomer); (Rp)-8-pCPT-cylic GMPS, TEA (Guanosine 3',5'-cyclic Monophosphorothioate, 8-(4-Chlorophenylthio)-, Rp-Isomer, Triethylammonium Salt); Rp-8-Br-cGMPS, Na (Guanosine 3',5'-cyclic Monophosphorothioate, 8-Bromo-, Rp-Isomer, Sodium Salt); DT-3, Antennapedia Homeodomain (43-58)-W45 fusion protein (the protein inhibitor consisting of the Antennapedia homeodomain fused with protein inhibitor W45, with the amino acid formula RQIKIWFQNRRMKWKK-LRKKKKKH); DT-2, HIV1-TAT-W45 fusion protein (the protein inhibitor consisting of the Human Immunodeficiency Virus 1 Membrane Translocation Sequence (47-59) fused with protein inhibitor W45, with the amino acid formula YGRKKRRQRRRPP-LRKKKKKH) and the protein inhibitor having the amino acid formula RKRARKE.

These PKG pathway inhibitors are commercially available; a leading supplier is Calbiochem (EMD) Biosciences.

The pharmacological inhibitor may be a cGMP-specific antagonist, i.e. a suitable antagonist might stimulate the activity of PDE5 or PDE9 in the breakdown of cGMP.

The pharmacological inhibitor may be an inhibitor of K+ ion channel function.

The pharmacological inhibitor may be a protein phosphatase inhibitor. Suitable protein phosphatase inhibitors include, for example, Okadaic acid, Microcystin, Calyculin, and Cantharidin (Hexahydro-3a,7a-dimethyl-4,7-epoxy-isobenzofuran-1,3 -dione).

The pharmacological inhibitor may be a sGC inhibitor, for example, 4H-8-Bromo-1,2,4-oxadiazolo(3,4-d)benz(b)(1,4)oxazin-1-one (NS 2028), 1H-[1,2,4]Oxadiazolo[4,3-a]quinoxalin-1-one (ODQ) or 6-Anilino-5,8-quinolinequinone (LY83583).

It will be recognized by those of skill in the art that certain of the aforementioned inhibitors are known in certain forms to have toxic effects, which must be addressed through formulation of the thermoprotective composition, as is known to those of skill in the art.

The neural thermoprotective composition of the present invention is suitable for treating a number of medical conditions including heat stroke; ischemia-induced hyperthermia; opioid (i.e. morphine) or anaesthetic induced hyperthermia; febrile seizure; and pre-existing conditions predisposing to hyperthermia, such as familial Malignant Hyperthermia (MH).

The manner of administering the thermoprotective composition of the present invention to a patient is not specifically restricted, and various methods will be readily apparent to persons skilled in the art. The thermoprotective composition, for example, could be delivered by injection or intravenously to a patient suffering from hyperthermia. The compound could be taken orally. This would be particularly suitable where it is taken as a prophylactic. For example, the composition could be used as an oral prophylactic to prevent heat stroke in emergency or military personnel who must work in the heat.

Where the term "patient" is used in the present specification, it will be understood to include both human and non-human patients, including animals and plants.

While this invention has been described with reference to illustrative embodiments and examples, the description is not intended to be construed in a limiting sense. Thus, various modifications of the illustrative embodiments, as well as other embodiments of the invention will be apparent to persons skilled in the art upon reference to this description. For example the modification of inhibitors to improve solubility and cell permeability through packaging with modifying agents such as Membrane Translocation Proteins, esterification such that the esterified compound passes through lipid membranes and is converted into the active form in the cell by constitutive esterases, and the use of alternative salts of acid or basic compounds to improve solubility, stability, or buffer pH changes are apparent to persons skilled in the art upon reference to this description as means of improving stability, solubility, and delivery to the cell of the pharmacological inhibitors.

All publications, patent and patent applications referred to herein are incorporated by reference in their entirety to the same extent as if each individual publication, patent or patent application was specifically and individually indicated to be incorporated by reference it its entirety.

EXAMPLES

Example 1

D. Melanogaster Experiments:

The foraging (for) gene in *Drosophila melanogaster* encodes a cGMP-dependent protein kinase (PKG) (Osborne, K. A. et al., 1997). Evoked synaptic transmission was measured at the neuromuscular junction (NMJ) of $3^{rd}$ instar foraging larvae in both high and low PKG activity strains (for$^R$ and for$^{s2}$ respectively).

Figure 1A:
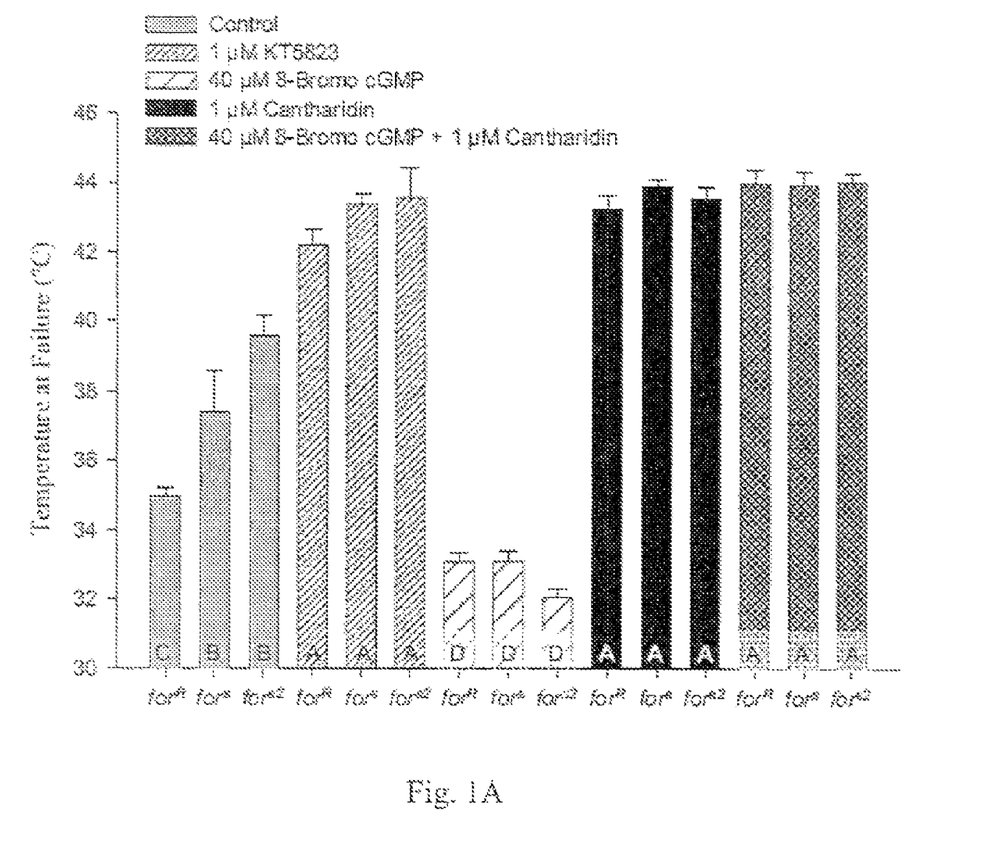
FIGS. 1A and 1B illustrate hyperthermic failure of evoked excitatory junction potential (EJP) failure at the NMJ.
Figure 1B:
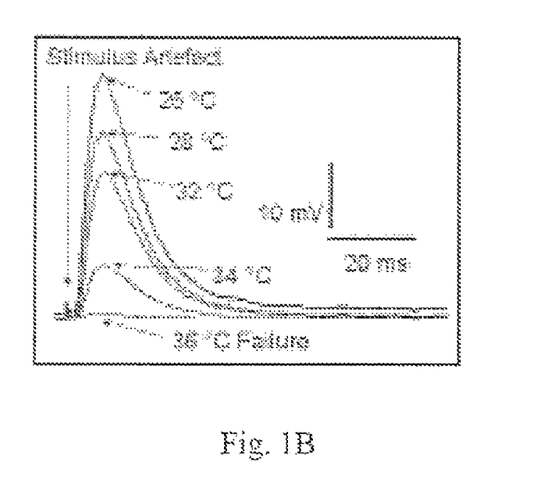

FIGS. 1A and 1B illustrate hyperthermic failure of evoked excitatory junction potential (EJP) failure at the NMJ (N>5 for all genotype and treatment combinations). Increased temperature sensitivity of evoked synaptic transmission correlated with genotype, where significant differences were found across groups ($F_{(14,100)}$=76.95, p<0.001). The involvement of PKG activity was verified using pharmacological agents to activate PKG (40 μM 8-Bromo cGMP), inhibit PKG (1 μM KT5823) or inhibit a PKG phosphorylation target PP2A (1 μM Cantharidin). A combination of 8-Bromo cGMP and Cantharidin was also used, demonstrating that Cantharidin likely acts downstream of PKG activation. Letters in histogram bars represent statistical groupings using a post-hoc test, whereby bars with different letters are significantly different (Tukey p<0.05). Error bars represent SEM.

Thus, both genetic and pharmacological manipulations demonstrate that there is a negative relationship between PKG activity and thermotolerance at the *D. melanogaster* larval NMJ.

96±2 hr. for aging for$^R$ and for$^{s2}$ $3^{rd}$ instar *D. melanogaster* larvae reared on a yeast-sugar-agar medium at 24±1° C. under 12L: 12D light cycle were pinned on a glass dish, and dissected to reveal segmental muscles and their corresponding nerves. Nerves in segment 3 or 4 were stimulated via a suction electrode, and the corresponding excitatory junction potential (EJP) recorded from muscle 6 with an intracellular electrode (40-80 MΩ). The preparation was superfused with HL-6 saline with 1 mM $[Ca^{2+}]_e$ and heated at a rate of ~5° C./min. from room temperature (23° C.) to synaptic failure. Preparations treated with the PKG inhibitor KT5823 or the cGMP analogue 8-bromo-guanosine 3',5'-cyclic monophosphate (8-br-cGMP) were bathed with the compound of interest for 5 min. prior to starting the superfusion of saline. KT5823 was dissolved in DMSO for a 0.2% (v/v) concentration in saline during treatment. for$^{s2}$ was generated on a for$^R$ genetic background.

Figure 2:
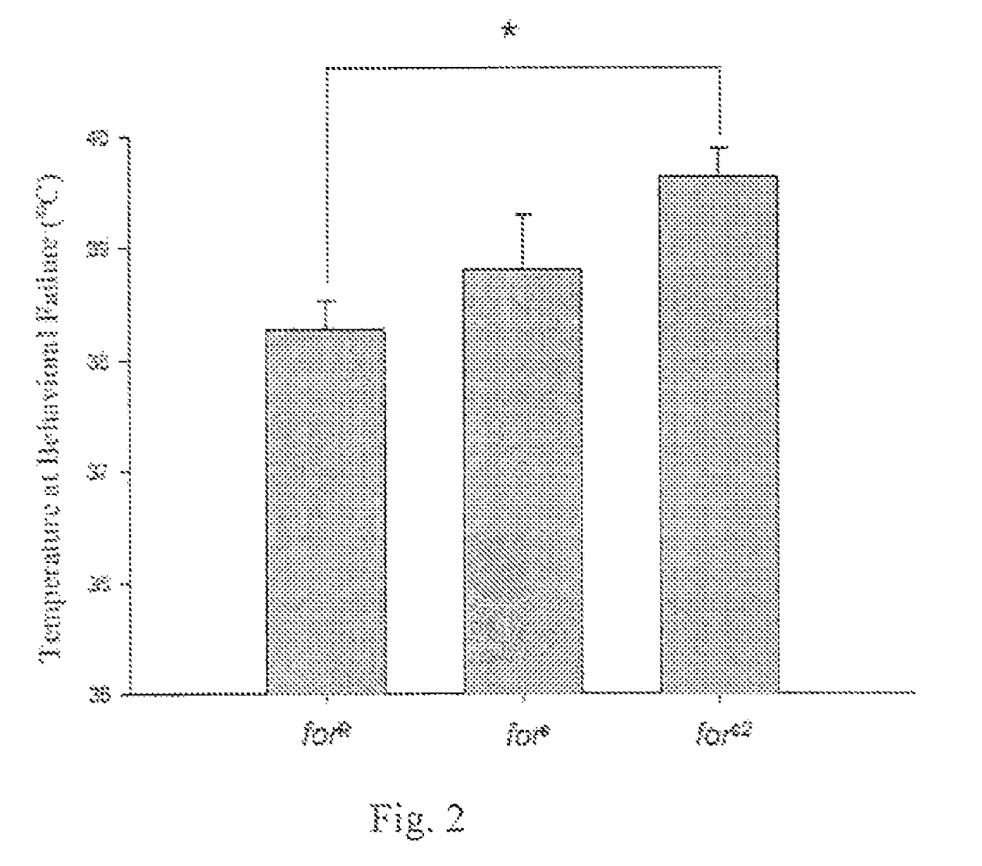

FIGS. 1 to 2 illustrate hyperthermic failure of both behaviour and NMJ synaptic transmission in $3^{rd}$ instar for$^R$, for$^s$ and for$^{s2}$ *Drosophilia* larvae.

As shown in FIG. 2, higher temperature at behavioral failure of mouth hook movement is correlated with genotype: for$^R$ failed at 38.2° C.±0.3 (N=10), for$^s$ failed at 38.8° C.±0.5 (N=11) and for$^{s2}$ failed at 39.6° C.±0.3 (N=11). Significant differences were found across groups ($F_{(2,26)}$=5.82, p=0.009) where asterisks denote significant differences using a post-hoc test (Tukey, p<0.05).

Example 2

L. Miratoria Experiments

Figure 3:
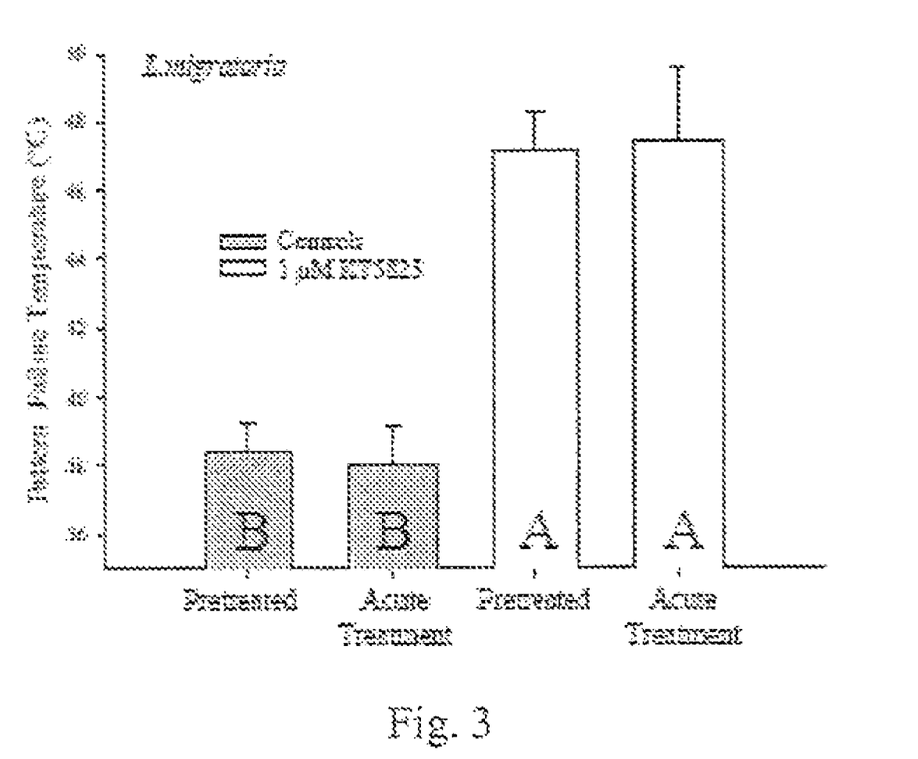
FIG. 3 illustrates motor pattern failure with increasing temperature of the ventilatory rhythm in adult locusts in pretreated (25 nl of saline [control] or KT5823 10 min. before temperature ramp) and acutely treated (25 nl of saline [control] or KT5823 ~3 min. before failure during temperature ramp) animals.
Figure 4:
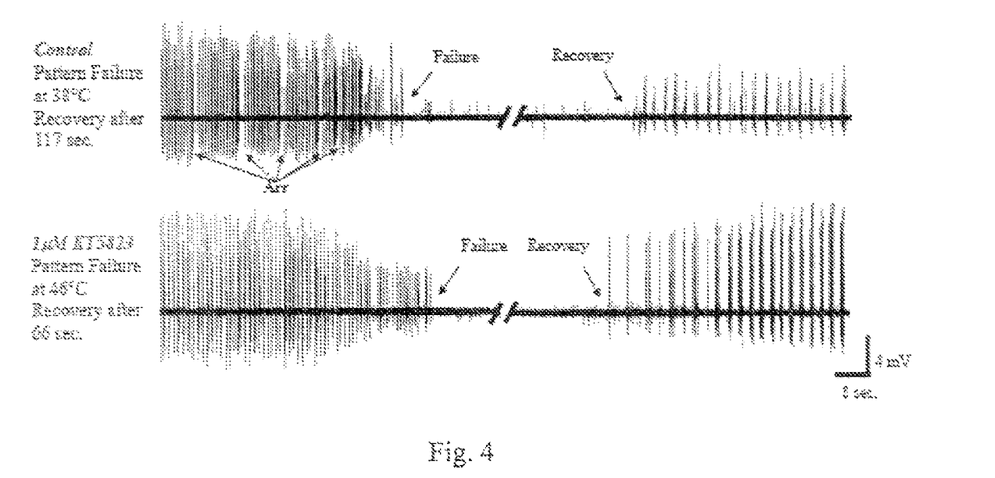
FIG. 4 illustrates sample traces of the ventilatory rhythm recorded from an abdominal expiratory muscle in control and KT5823-treated locusts.
Figure 5:
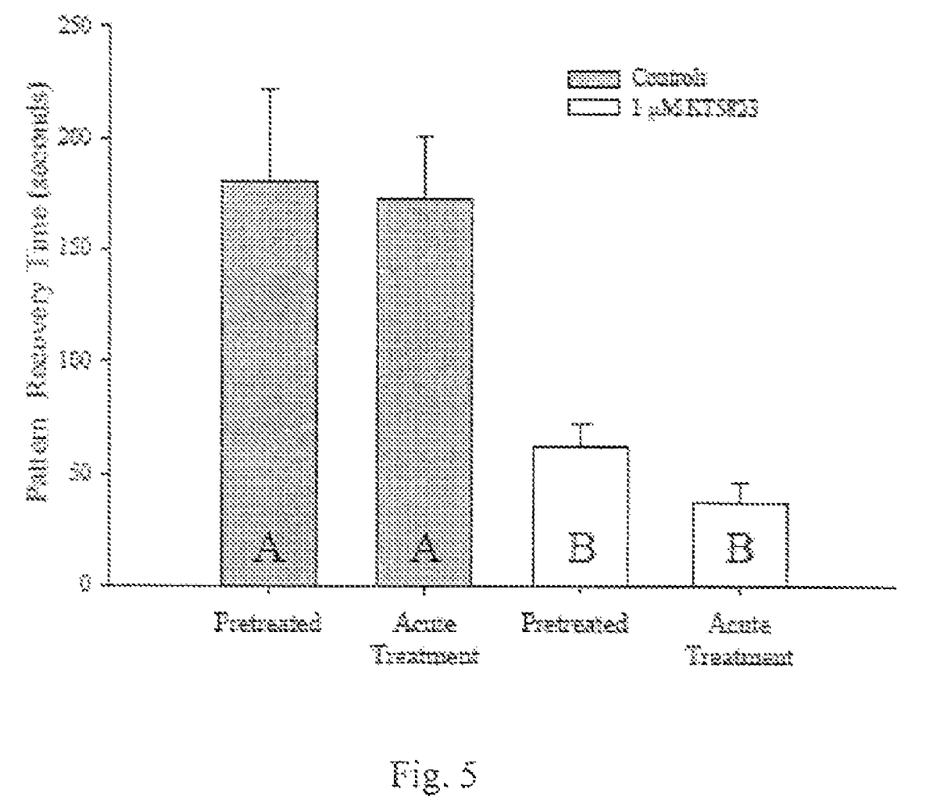
FIG. 5 illustrates recovery time of ventilatory motor pattern after failure in locusts.

To determine if the thermoprotective consequences of PKG manipulations also apply to central circuitry and motor pattern generation, the thermotolerance of the ventilatory pattern generator was measured (Robertson, R. M. 2004) of the locust, Locusta migratoria. (25 nL) of 1 µM KT5823 was pressure injected into the neural circuit for ventilation 10 minutes before increasing temperature and thermoprotection and rapid recovery of the circuit was observed (FIGS. 3, 4, 5). Additionally, one 25 nL dose of KT5823 was injected into untreated animals during the temperature ramp only 3 min. before failure and an extremely rapid and equally pronounced thermal protection of the circuit was observed (FIG. 3; Pretreated controls (N=6) and acutely treated controls (N=3) significantly differ from the 1 µM KT5823 pretreated (N=8) and acutely treated animals (N=5)). Ventilatory arrhythmias (Arr) in untreated animals prior to hyperthermic failure are rarely seen in preparations treated with the PKG inhibitor (FIG. 4.). At failure, temperature was returned to room temperature and time to recovery recorded. Pretreated controls recover after 180.2±42.4 sec whereas KT5823-pretreated animals recover after 62.3±13.4 sec. After recovery, the ventilatory motor patterns exhibit a slower rhythm than just prior to failure because the temperature is lower at this time point. Once ventilatory pattern failure occurs during a temperature ramp, heating was terminated and the motor pattern was monitored until recovery. Pretreated (25 nl of saline [control] or KT5823 10 min. before temperature ramp; N=6) and acutely treated (25 nl of saline [control] or KT5823~3 min. before failure during temperature ramp; N=3) controls took significantly longer to recover compared to the pretreated (N=8) and acutely treated (N=5) KT5823 animals (FIG. 5).

Figure 6:
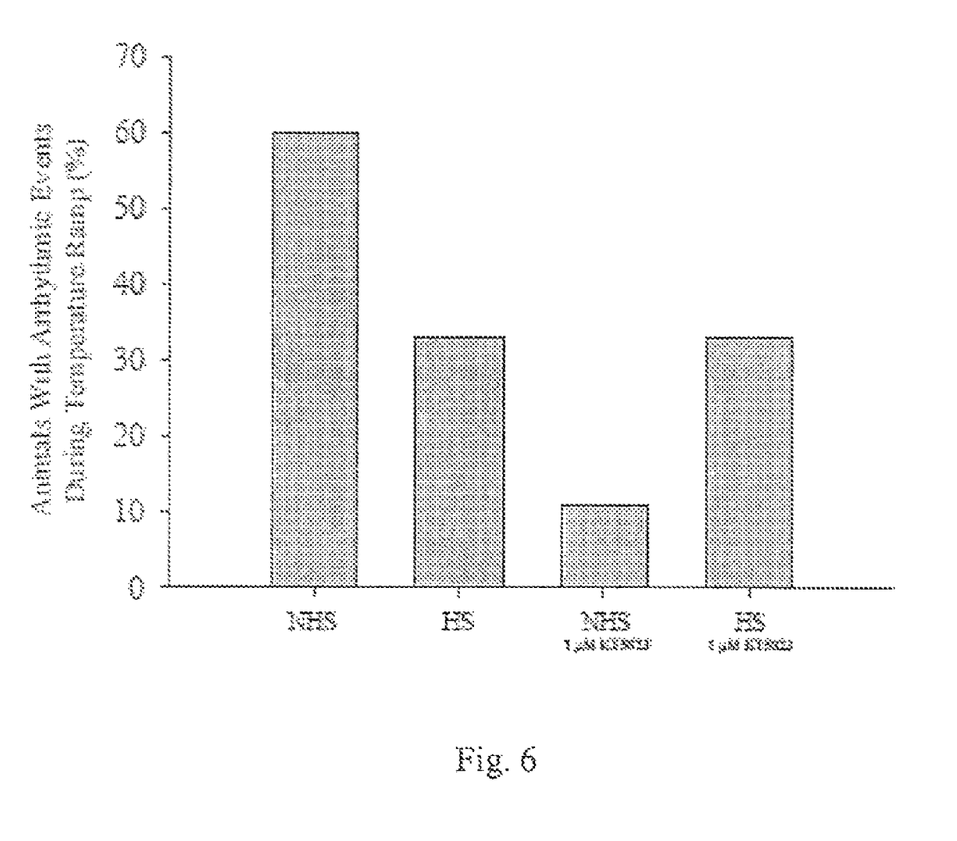

When the PKA inhibitor RP-cAMP was used and compared with controls, no significant differences in failure temperature or recovery time was seen (data not shown). Interestingly, robust rhythms with few arrhythmias occur until failure in KT5823-treated preparations (11%) compared with controls (60%). Furthermore, rapid thermoprotection via PKG inhibition was comparable to the gradually induced protective effects of previously reported heat shock pretreatments (FIG. 6).

Male locusts aged 4-6 weeks were dissected and pinned on a cork board; overlying tissue was removed exposing the metathoracic ganglion. Standard locust saline was superfused and heated at a rate of 5° C./2 min. until motor pattern failure, after which saline was allowed to return to room temperature. Ventilatory motor patterns were monitored using an EMG electrode on muscle 161 in the second abdominal segment. Pressure injection (32±13.5 nL, 10 psi, 150 ms) into the ventilatory neuropil was with a glass microelectrode filled with either 1 µM KT5823 in standard locust saline or locust saline alone (sham treatment) 10 min. (pretreated) before, or during (acutely treated; ~3 min. before failure in controls) the temperature ramp. Injection of KT5823 had no acute effect on ventilatory rhythm frequency, burst duration or duty cycle (data not shown).

Figure 7A:
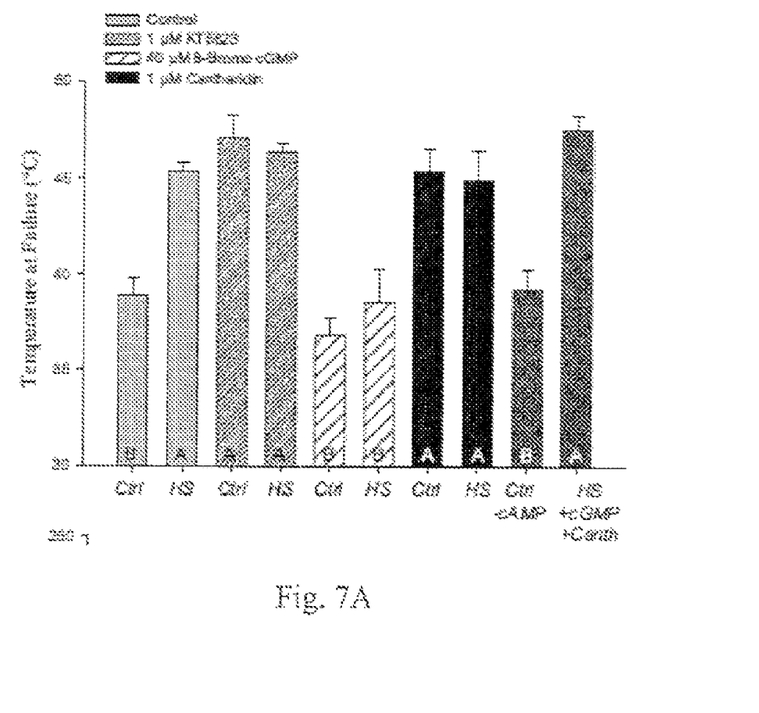
FIG. 7A illustrates the increase in thermotolerance of neural function with reduction in either PKG activity (1 µM KT5823) or PP2A activity (1 µM Canthardin). Activation of PKG using 40 µM 8-Bromo cGMP did not increase the thermotolerance of the circuit, but abolished the protective effects of heat shock preconditioning. The PP2A inhibitor Canthardin counteracted the effect of 8-Bromo cGMP in HS animals thereby inducing maximal thermotolerance. –cAMP, +cGMP and +Canth correspond to cAMP inhibitor (1 µtM Rp-cAMP), cGMP agonist (40 µM 8-Bromo cGMP) and PP2A inhibitor (1 µM Canthardin).
Figure 7B:
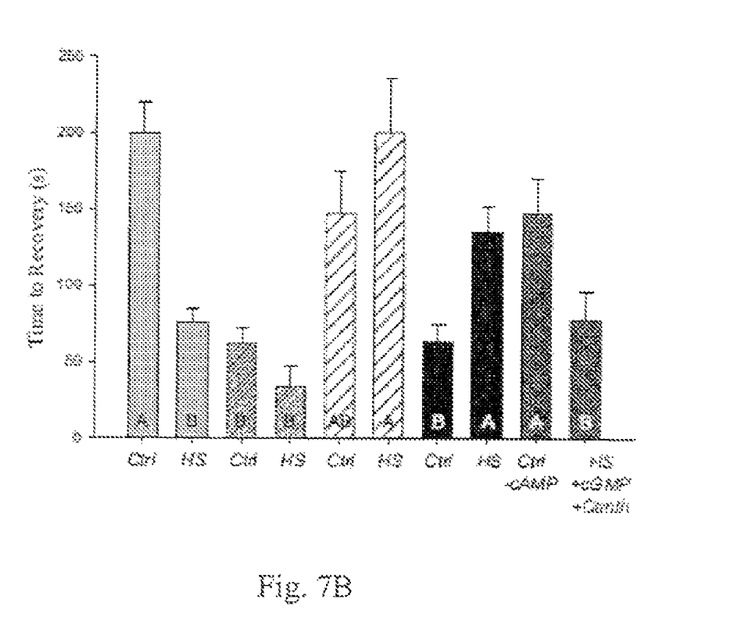
FIG. 7B illustrates recovery time of the motor pattern upon return to room temperature.
Figure 8:
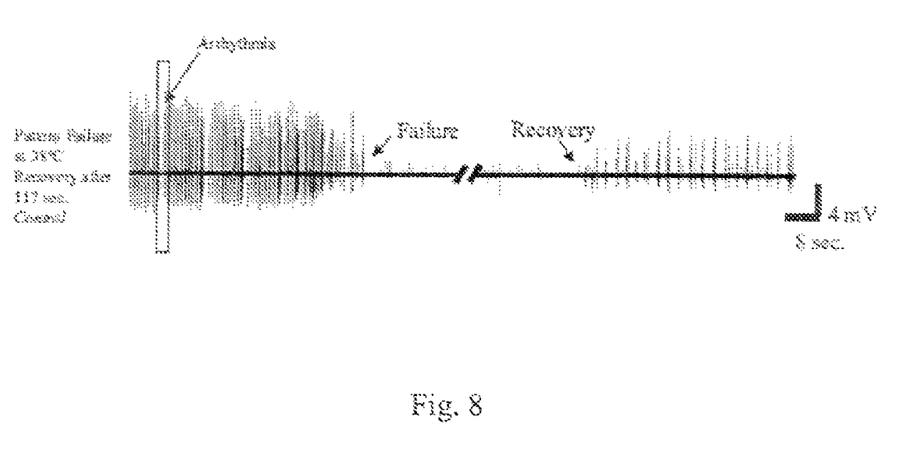
FIG. 8 illustrates sample traces of the ventilatory rhythm recorded from an abdominal expiratory muscle in a control locust.

FIGS. 7 to 8 illustate hyperthermic failure of locust ventilatory motor pattern generation. FIG. 8 illustrates sample traces of the ventilatory rhythm recorded from an abdominal expiratory muscle in a control locust. The ventilatory arrhythmias prior to failure should be noted. At failure, temperature was allowed to return to room temperature and time to recovery was recorded. The ventilatory motor pattern after recovery is at a lower frequency than just prior to failure because the temperature is lower. As shown in FIG. 7A, reduction in either PKG activity (1 µM KT5823) or PP2A activity (1 µM Cantharidin) increased the thermotolerance of neural function. Activation of PKG using 40 µM 8-Bromo cGMP did not increase the thermotolerance of the circuit, but abolished the protective effects of heat shock preconditioning. However, the PP2A inhibitor Cantharidin counteracted the effect of 8-Bromo cGMP in HS animals thereby inducing maximal thermotolerance. −cAMP, +cGMP and +Canth correspond to cAMP inhibitor (1 µM Rp-cAMP), cGMP agonist (40 µM 8-Bromo cGMP) and PP2A inhibitor (1 µM Cantharidin). Significant differences were found across all groups (ANOVA $F_{(9,105)}$=13.160, p<0.001). As illustrated in FIG. 7B recovery time of the motor pattern upon return to room temperature showed corresponding differences in the same treatment groups (short recovery times were associated with high failure temperatures in 7A). Here too significant differences were found across all groups (ANOVA $F_{(105,9)}$=8.63, p<0.001) N>5 for all treatments. Letters in histogram bars represent statistical groupings whereby bars with different letters are significantly different using a post-hoc test (Tukey, p<0.05). Error bars represent SEM.

REFERENCES

Canini, F., Bourdon, L., Cespuglio, R. and Buguet, A. (1997) Voltametric assessment of brain nitric oxide during heatstroke in rats. Neurosci. Lett., 231, 67-70.

Canini, F., Buguet, A. and Bourdon, L. (2001) Inhibition of different types of nitric oxide synthase: effect on thermoregulation in the rat exposed to high ambient temperature. Neurosci. Lett., 316, 45-49.

Chang, C. P., Lee, C. C., Chen, S. H. and Lin, M. T. (2004) Aminoguanidine protects against intracranial hypertension and cerebral ischemic injury in experimental heatstroke. J. Pharmacol. Sci., 95, 56-64.

Corbin, J. D. and Francis, S. H. (1999) Cyclic GMP Phosphodiesterase-5: Target of Sildenafil. J. Biol. Chem., 274, 13729-13732.

Dostmann, W. R., Tegge, W., Frank, R., Nickl, C. K., Taylor, M. S. and Brayden, J. E. (2002) Exploring the mechanisms of vascular smooth muscle tone with highly specific, membrane-permeable inhibitors of cyclic GMP-dependent protein kinase 1alpha. Pharmacol. Ther., 93, 203-215.

Fitzpatrick, M. J. and Sokolowski, M. B. (2004) In Search of food: Exploring the evolutionary link between cGMP-dependent protein kinase (PKG) and behaviour. Integr. Comp. Biol., 44, 28-36

Gerstberger, R. (1999) Nitric Oxide and Body Temperature Control. News Physiol. Sci., 14, 30-36.

Glazer, J. L. Am Fam Physician. 71; 11 2133 (2005).

Gulec, G. and Noyan, B. (2001) Do recurrent febrile convulsions decrease the threshold for pilocarpine-induced seizures? Effects of nitric oxide. Brain Res. Dev. Brain Res., 126, 223-228.

Gurnett, A. et al., (20020 J. Biol. Chem. 277: 15913-15922.

Jayakar, S. S. and Dikshit, M. (2004) AMPA receptor regulation mechanisms: future target for safer neuroprotective drugs. Int. J. Neurosci., 114, 695-734.

Klyueva, Y. A., Bashkatova, V. G., Vitskova, G. Y., Narkevich, V. B., Mikoyan, V. D., Vanin, A. F., Chepumov, S. A. and Chepumova, N. E. (2001) Role of nitric oxide and lipid peroxidation in mechanisms of febrile convulsions in Wistar rat pups. Bull. Exp. Biol Med., 131, 47-49.

Liu, L., Yang, T., Bruno, M. J., Andersen, O. S. and Simon, S. A. (2004) Voltage-Gated Ion Channels in Nociceptors: Modulation by cGMP. *J. Neurophysiol.*, 92, 2323-2332.

Osborne, K. A. et al., (1997) *Science*. 277, 834.

Patel, A. I. and Diamond, J. (1997) Activation of Guanosine 3', 5'-Cyclic Monophosphate (cGMP)-Dependent Protein Kinase in Rabbit Aorta by Nitroglycerin and Sodium Nitroprusside. *J. Pharmacol. Exp. Ther.*, 283, 885-893.

Ramirez, J. M., Elsen, F. P. and Robertson, R. M. (1999) Long-term effects of prior heat shock on neuronal potassium currents recorded in a novel insect ganglion slice preparation. *J. Neurophysiol.*, 81, 795-802.

Renger, J. J. et al., *J Neurosci.* 19, RC28 (1999).

Robertson, R. M. (2004) Thermal stress and neural function: adaptive mechanisms in insect model systems. *Journal of Thermal Biology*, 29, 351-358.

Sachidhanandam, S. B., Low, K. S. and Moochhala, S. M. (2002) Naltrexone attenuates plasma nitric oxide release following acute heat stress. *Eur. J. Pharmacol*, 450, 163-167.

Sandberg, M., et al., FEBS Lett (1989) 251, 191-196.

Schiffmann, Desdouits, Menu, Greengard, Vincent, J., Vanderhaeghen, J. and Girault, J. (1998) Modulation of the voltage gated sodium current in rat striatal neurons by DARPP 32, an inhibitor of protein phosphatase. *Eur. J. Neurosci.*, 10, 1312-1320.

Somjen, G. G. (2002) Ion regulation in the brain: implications for pathophysiology. *Neuroscientist*, 8, 254-267.

Somjen, G. G. (2001) Mechanisms of spreading depression and hypoxic spreading depression-like depolarization. *Physiol. Rev.*, 81, 1065-1096.

Taylor, M. S., Okwuchukwuasanya, C., Nickl, C. K., Tegge, W., Brayden, J. E. and Dostmann, W. R. (2004) Inhibition of cGMP-dependent protein kinase by the cell-permeable peptide DT-2 reveals a novel mechanism of vasoregulation. *Mol. Pharmacol.*, 65, 1111-1119.

Tryba, A. K. and Ramirez, J. M. *Neurophysiol.* 92, 2844 (2004).

Wang, J., Zhou, Y., Wen, H. and Levitan, I. B. (1999) Simultaneous binding of two protein kinases to a calcium-dependent potassium channel. *J. Neurosci.*, 19, RC4.

Wang, J. W., Humphreys, J. M., Phillips, J. P., Hilliker, A. J. and Wu, C. F. (2000) A novel leg-shaking *Drosophila* mutant defective in a voltage-gated K(+)current and hypersensitive to reactive oxygen species. *J. Neurosci.*, 20, 5958-5964.

White, R. E. (1999) Cyclic GMP and ion channel regulation. *Advances in Second Messenger and Phosphoprotein Research*, 33, 251-277.

White, R. E., Lee, A. B., Shcherbatko, A. D., Lincoln, T. M., Schonbrunn, A. and Armstrong, D. L. (1993) Potassium channel stimulation by natriuretic peptides through cGMP-dependent dephosphorylation. *Nature*, 361, 263-266.

Zeng, H., Fei, H. and Levitan, I. B. (2004) The slowpoke channel binding protein Slob from *Drosophila* melanogaster exhibits regulatable protein kinase activity. *Neurosci. Lett.*, 365, 33-38.

Zhou, X. B., Ruth, P., Schlossmann, J., Hofmann, F. and Korth, M. (1996) Protein phosphatase 2A is essential for the activation of Ca2+-activated K+ currents by cGMP-dependent protein kinase in tracheal smooth muscle and Chinese hamster ovary cells. *J. Biol. Chem.*, 271, 19760-19767.

Zhou, X. B., Schlossmann, J., Hofmann, F., Ruth, P. and Korth, M. (1998) Regulation of stably expressed and native BK channels from human myometrium by cGMP- and cAMP-dependent protein kinase. *Pflugers Arch.*, 436, 725-734.

What is claimed is:

1. A method of providing neural thermoprotection to a patient in need thereof comprising administering to said patient in need of neural thermoprotection an amount of a pharmacological inhibitor of the PKG pathway effective to confer said protection upon said patient.

2. The method according to claim 1 wherein the neural thermoprotection results from a reduction in potassium ion channel conductances.

3. The method according to claim 1, wherein providing neural protection includes providing at least an effect selected from the group consisting of:
   increasing the temperature at which neural function becomes abnormal; increasing the time to abnormal neural function when exposed to heat; reducing the precursor symptoms of neural failure; reducing the time to recovery from abnormal neural function after treatment, wherein the abnormal neural function includes heat stroke, ischemia-induced hyperthermia, opioid or anaesthetic induced hyperthermia, febrile seizure, or pre-existing conditions predisposing to hyperthermia.

4. The method according to claim 3, wherein reducing the precursor symptoms of neural failure involves reducing arrhythmias.

5. The method according to claim 3, wherein the pharmacological inhibitor of the PKG pathway provides neural thermoprotection within 3 minutes after neural administration.

6. The method according to claim 3, wherein the pharmacological inhibitor of the PKG pathway is a PKG inhibitor.

7. The method according to claim 6, wherein the pharmacological inhibitor is selected from the group consisting of:
   KT5823;
   (Rp)-8-bromo-PET-cyclic GMPS;
   (Rp)-8-pCPT-cylic GMPS,TEA;
   Rp-8-Br-cGMPS, Na;
   DT-3, Antennapedia Homeodomain (43-58)-W45 fusion protein;
   DT-2, HIV1-TAT-W45 fusion protein,
   and mixtures thereof.

8. The method according to claim 3, wherein the pharmacological inhibitor is a cGMP-specific antagonist.

9. The method according to claim 3, wherein the pharmacological inhibitor inhibits K+ ion channel function.

10. The method according to claim 3, wherein the pharmacological inhibitor is a protein phosphatase inhibitor.

11. The method according to claim 10, wherein the protein phosphatase inhibitor is selected from the group consisting of Okadaic acid, Microcystin, Calyculin, and Cantharidin.

12. The method according to claim 3, wherein the pharmacological inhibitor is a sGC inhibitor.

13. The method according to claim 12, wherein the pharmacological inhibitor is selected from the group consisting of 4H-8-Bromo-1,2,4-oxadiazolo (3,4-d) benz(b)(1,4)oxazin-1-one, 1H-[1,2,4]Oxadiazolo [4,3-a]quinoxalin-1-one (ODQ) or 6-Anilino-5,8-quinolinequinone.

14. The method according to claim 3, wherein the abnormal neural function is opioid induced hyperthermia and the opioid is morphine.

15. The method according to claim 3, wherein the abnormal neural function is a pre-existing condition predisposing to hyperthermia and the condition is familial Malignant Hyperthermia (MH).

* * * * *